United States Patent
Dickopf et al.

(10) Patent No.: US 7,842,242 B2
(45) Date of Patent: Nov. 30, 2010

(54) OPTICAL COUPLING DEVICE AND METHOD

(75) Inventors: Stefan Dickopf, Heidelberg (DE); Thomas Perschke, Bammental (DE); Mladen Nedic, Waldsee (DE); Kristina Schmidt, Schriesheim (DE)

(73) Assignee: Graffinity Pharmaceuticals AG, Heidelberg (DE)

(*) Notice: Subject to any disclaimer, the term of this patent is extended or adjusted under 35 U.S.C. 154(b) by 805 days.

(21) Appl. No.: 10/555,818

(22) PCT Filed: Apr. 1, 2004

(86) PCT No.: PCT/EP2004/003455

§ 371 (c)(1),
(2), (4) Date: Jun. 6, 2007

(87) PCT Pub. No.: WO2004/099762

PCT Pub. Date: Nov. 18, 2004

(65) Prior Publication Data

US 2007/0248300 A1    Oct. 25, 2007

(30) Foreign Application Priority Data

May 5, 2003    (DE)    ................. 103 20 226

(51) Int. Cl.
*G01N 21/00*    (2006.01)
*G02B 6/26*    (2006.01)
*G01N 21/55*    (2006.01)

(52) U.S. Cl. .............. 422/82.05; 385/15; 356/445
(58) Field of Classification Search .......... 422/82.05; 385/15
See application file for complete search history.

(56) References Cited

U.S. PATENT DOCUMENTS

| 4,934,818 A | 6/1990 | Glantschnig et al. |
| 5,164,589 A | 11/1992 | Sjödin |
| 5,763,191 A * | 6/1998 | Knoll et al. ............. 435/7.1 |
| 6,752,963 B2 | 6/2004 | Dickopf et al. |
| 6,870,627 B2 * | 3/2005 | Elkind et al. .......... 356/445 |
| 2001/0026943 A1 | 10/2001 | Dickopf et al. |

FOREIGN PATENT DOCUMENTS

| DE | 2621895 | 12/1977 |
| EP | 0863395 | 9/1998 |
| WO | WO 01/63256 | 8/2001 |

* cited by examiner

*Primary Examiner*—Jill Warden
*Assistant Examiner*—Bryan T Kilpatrick
(74) *Attorney, Agent, or Firm*—Fitch, Even, Tabin & Flannery

(57) ABSTRACT

A device for optically coupling a first optical element to a second optical element comprises a first optical element with a first radiation penetration surface; a second optical element with a second radiation penetration surface located across from the first radiation penetration surface; and a chamber delimited by the first and second radiation penetration surfaces and a circumferentially closed side wall which connects the first and second radiation penetration surfaces. The circumferentially closed side wall defines a first sector in the first radiation penetration surface and a second sector in the second radiation penetration surface, the area of the first sector being smaller than the area of the first radiation penetration surface, and the area of the second sector being smaller than the area of the second radiation penetration surface. The device further comprises a feeding conduit to the chamber for delivering index-adjusting liquid; and a discharge conduit from the chamber for evacuating index-adjusting liquid or gas from the chamber.

11 Claims, 9 Drawing Sheets

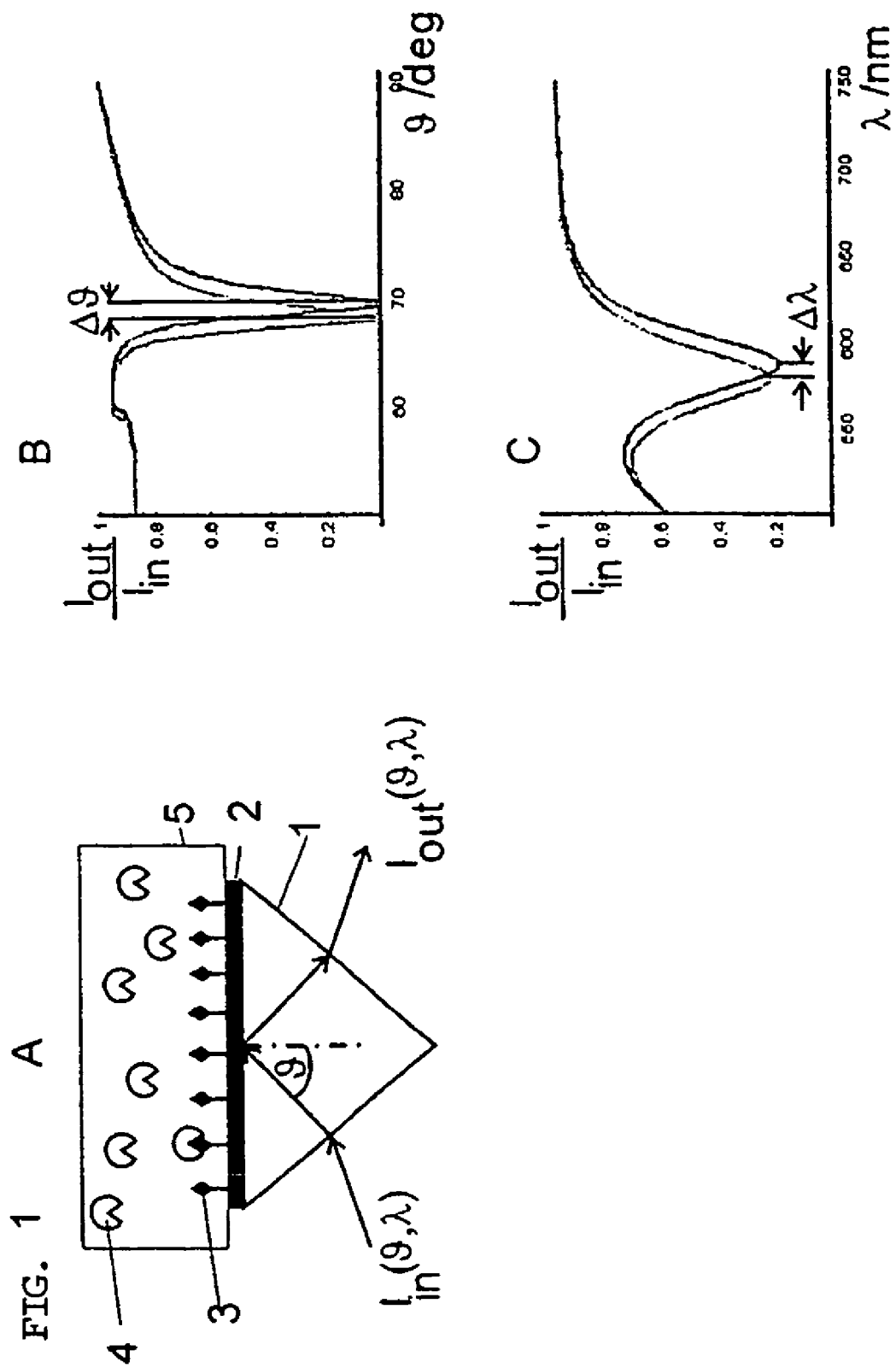

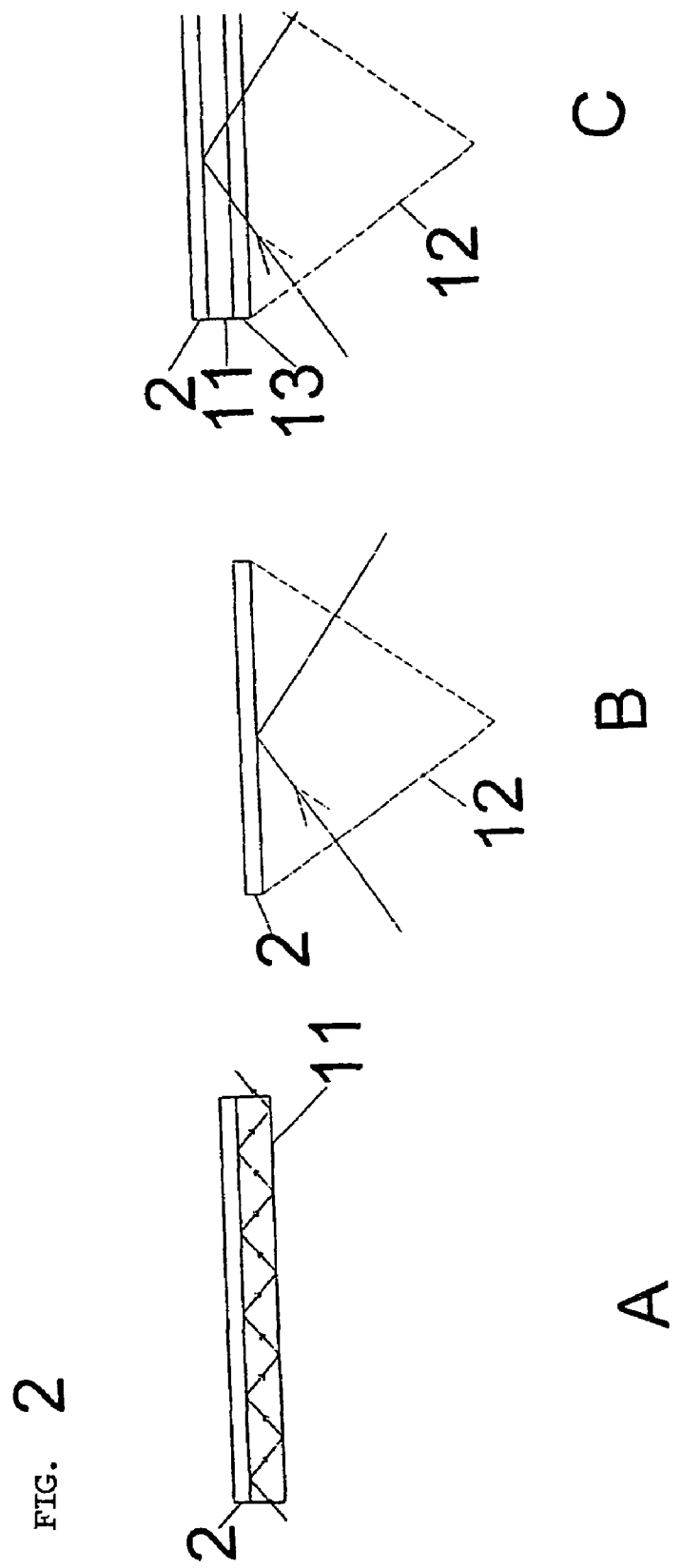

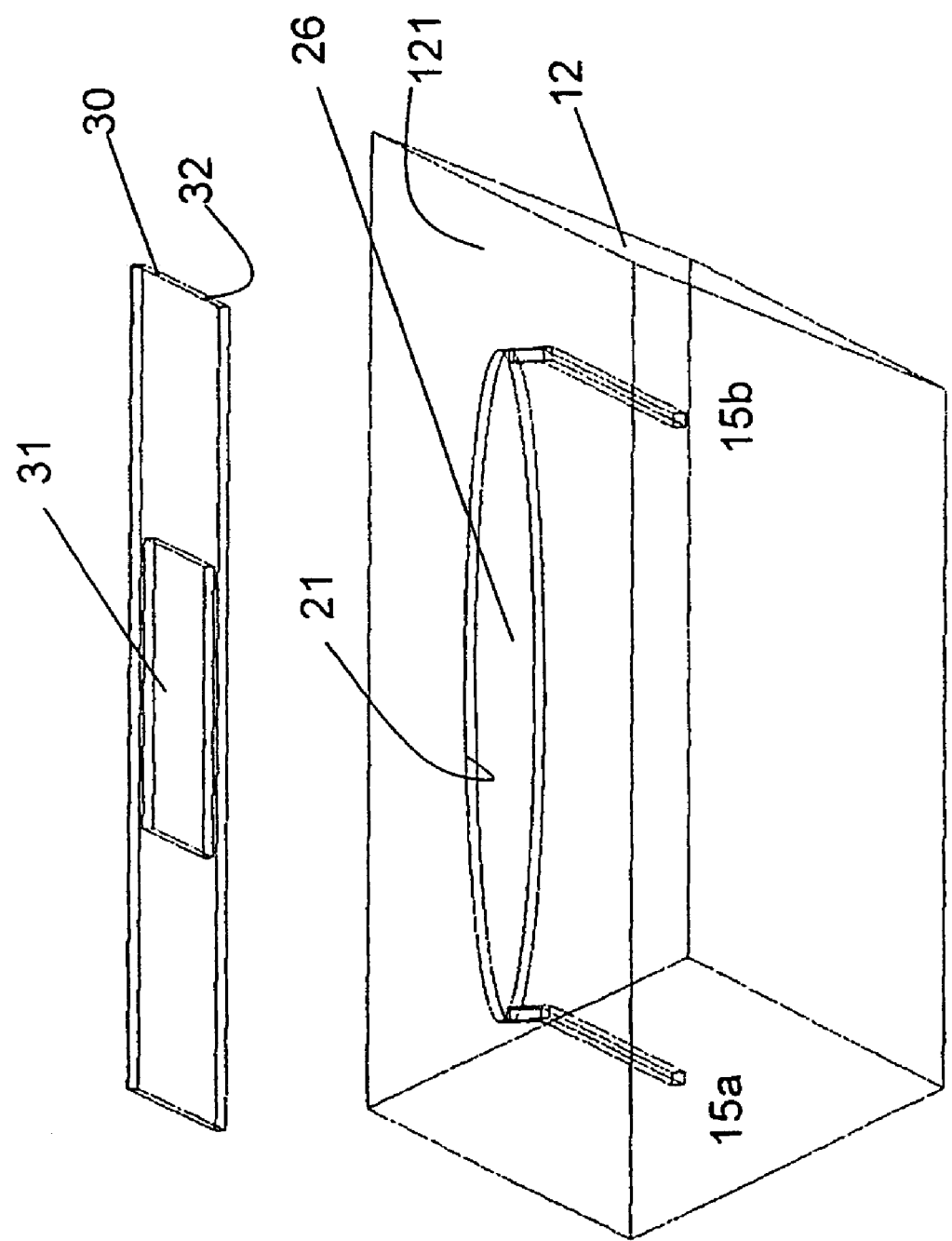

OPTICAL COUPLING DEVICE AND METHOD

The present invention relates to a device and a method for optically coupling a first optical element to a second optical element.

It is known in the field of optical metrology to insert means for index adaptation between separate optical elements such as, for example, a beam guiding member, on the one hand, and a sample carrier, on the other hand, such that the transition of optical radiation from one optical element to the other can occur with the least possible loss. The term "index adaptation" means here the adaptation of the refractive index.

An example of a measurement system in which such index-adapting means are used are SPR measurements. SPR stands for "Surface Plasmon Resonance".

SPR technology is an established method for marker-free detection of receptor-ligand interaction. This will be briefly explained with reference to FIG. 1A. In SPR, a glass substrate 1 is usually coated with a thin gold film 2, and one of the binding partners 3 is chemically immobilized on this gold surface (e.g., proteins are immobilized using a gel, or small molecules are immobilized on the surface by means of self-assembled monolayers (SAM)). The second binding partner 4, dissolved in the liquid 5, i.e. as sample liquid, is brought into wetting contact with the chemically modified gold surface. If the dissolved partner binds to the partner immobilized on the surface, the refractive index in the liquid layer right above the gold surface changes.

This refractive index change can be detected by means of plasmon resonance: Light is shone in through the glass substrate and is reflected at the gold layer. Under specific physical boundary conditions (angle of reflection, angle of polarization and radiation wavelength, refractive index of substrate and liquid, thickness of the gold layer), the light is not, however, reflected but absorbed. It is then that plasmon resonance occurs, i.e. the light energy is converted to an electron charge density wave along the gold/liquid interface. In practice, one of the two physical parameters of the light, i.e. angle of incidence (FIG. 1B) or wavelength (FIG. 1C), is now tuned and the intensity of the reflected light is detected as a function of this parameter. By this means, a reflection spectrum is obtained in which a drop in intensity (so-called SPR dip, see FIGS. 1B and 1C) can be observed once the resonance condition is reached. The minimum of this intensity drop is displaced once the refractive index of the liquid layer above the gold changes owing to the bonding of the reaction partner. It can be proven (for example, by way of experiment) that this displacement of the minimum ($\Delta\theta$ or $\Delta\lambda$) is directly proportional to the surface density of the bound molecules.

To technically implement this measuring process, use is commonly made of the so-called Kretschmann geometry (FIG. 1A). The reflection angle at which resonance occurs (the reflection angle for SPR with gold on glass and aqueous solutions is approx. 65-70° C.) lies, however, above the total reflection angle for the glass/air interface, i.e. in the case of a substrate in the form of a thin glass plate 11, the light cannot be shone in from the underside of the glass since no angle of incidence exists which after refraction of the light would result in an angle suitable for SPR. Furthermore, light which is reflected at the gold layer at an SPR angle does not leave the substrate but is rather directed within the substrate by means of multiple total reflection and can therefore no longer be detected in a spatially resolved manner (see FIG. 2A). Therefore, a prism 12 is used in the Kretschmann system which allows the light to penetrate into its side window at a small or entirely negligible angle of incidence and to then be reflected at the gold layer 2 at the angle large enough for SPR before exiting again from the other side window (see FIG. 2B).

Since it is disadvantageous economically to employ a new prism for each experiment, thin glass substrates 11 are normally used which carry the gold sensor surface 2 and are placed on top of a prism that can always be reused, with the gap between prism and glass substrate being filled with an index-adapting layer 13 (see FIG. 2C).

The index-adapting layer can be implemented in several possible ways, i.e. as
  a liquid index oil which runs into a thin capillary gap, or
  a thin layer of resilient silicone material (index matching rubber) as described, for example, in WO 97/19375.

Both methods have disadvantages associated therewith, in particular as regards large-surface sensor plates:

In the case of the oil method, the only possibility of removing the oil from the capillary gap is to open the capillary gap and to carry out a manual cleaning process. Also, air bubbles sometimes materialize when the capillary gap is being filled. The capillary gap must moreover be opened again to remove these bubbles.

The method with the index rubber presents a problem in the case of flat substrates since air bubbles tend to be trapped therein even if the rubber has a structure which expels the air in a defined manner when being pressed against. Total reflection occurs at the locations of the bubbles, and the location beneath on the sensor surface is then not visible.

If a bubble materializes in the rubber layer, it must be assumed that this has something to do with unevenness (the rubber mat does not fit at all points exactly between glass plate and prism). Thus, a new rubber mat must be used, on the flatness/homogeneity of which high demands are placed. This is very disadvantageous.

The problems described above are not limited to SPR measurement systems, they rather occur in general when the attempt is made to adapt the index between two optical elements. It should be noted that for purposes of the present description and the present claims, the term "optical" refers to any radiation capable of being passed through appropriate elements, i.e. is not limited to the visible range of the electromagnetic spectrum.

The object of the present invention is to provide an improved device and an improved method for optically coupling two separate elements.

This object is solved by a device having the features of claim 1 and a method having the features of claim 13. Preferred embodiments are described in the dependent claims.

According to the present invention, an index-adapting liquid is used as an index-adapting means, however, no capillary gap is employed. The present invention rather provides the formation of a chamber formed by radiation penetration surfaces of a first and a second optical element to be coupled, and is delimited by a circumferentially closed side wall which connects the two radiation penetration surfaces. Also provided is a feeding conduit for supplying index-adapting liquid into the chamber, as well as a discharge conduit for evacuating index-adapting liquid from the chamber. Thus, the chamber represents some sort of flow cell for the index-adapting liquid (e.g. index oil), with the liquid transportation being determined, at least not to a dominant extent, by capillary forces. It is possible by this means to easily and reliably achieve an optical coupling between the first and the second optical element by filling index-adapting liquid into the chamber via the feeding conduit. It is possible thereby to avoid, on the one hand, the problems arising with capillary gaps, since the chamber is dimensioned such that the index-adapting liquid can easily flow between the feeding conduit and the discharge conduit, and, on the other hand, the problems associated with index-adapting rubbers, since it is not a solid that is selected as the index-adapting means. The present invention offers in particular the advantage of being easily automatable as the index-adapting liquid can be supplied into and evacuated from the chamber by means of an automatic control system.

According to a preferred embodiment, a tilting means is provided so that the entire system can be brought into a tilted position in which the point at which index-adapting liquid is supplied into the chamber is disposed at a lower level, as viewed in the direction of gravity, than a point of discharge and/or air escape. By this means, bubble-free filling of the chamber is particularly simple since the air or gas bubbles rise upward and are expelled through the air escape point situated farther above by the index-adapting liquid supplied from below, whereas no bubbles are left in the index-adapting liquid.

The present invention will now be described in more detail with reference to the accompanying drawings in which:

FIG. 1 is a schematic diagram showing a prism and a sensor as well as measuring curves explaining the principle of surface plasmon resonance;

FIG. 2 shows schematic elements for SPR measurements;

FIG. 7 shows a further embodiment of the device according to the invention.

Figure 3A:
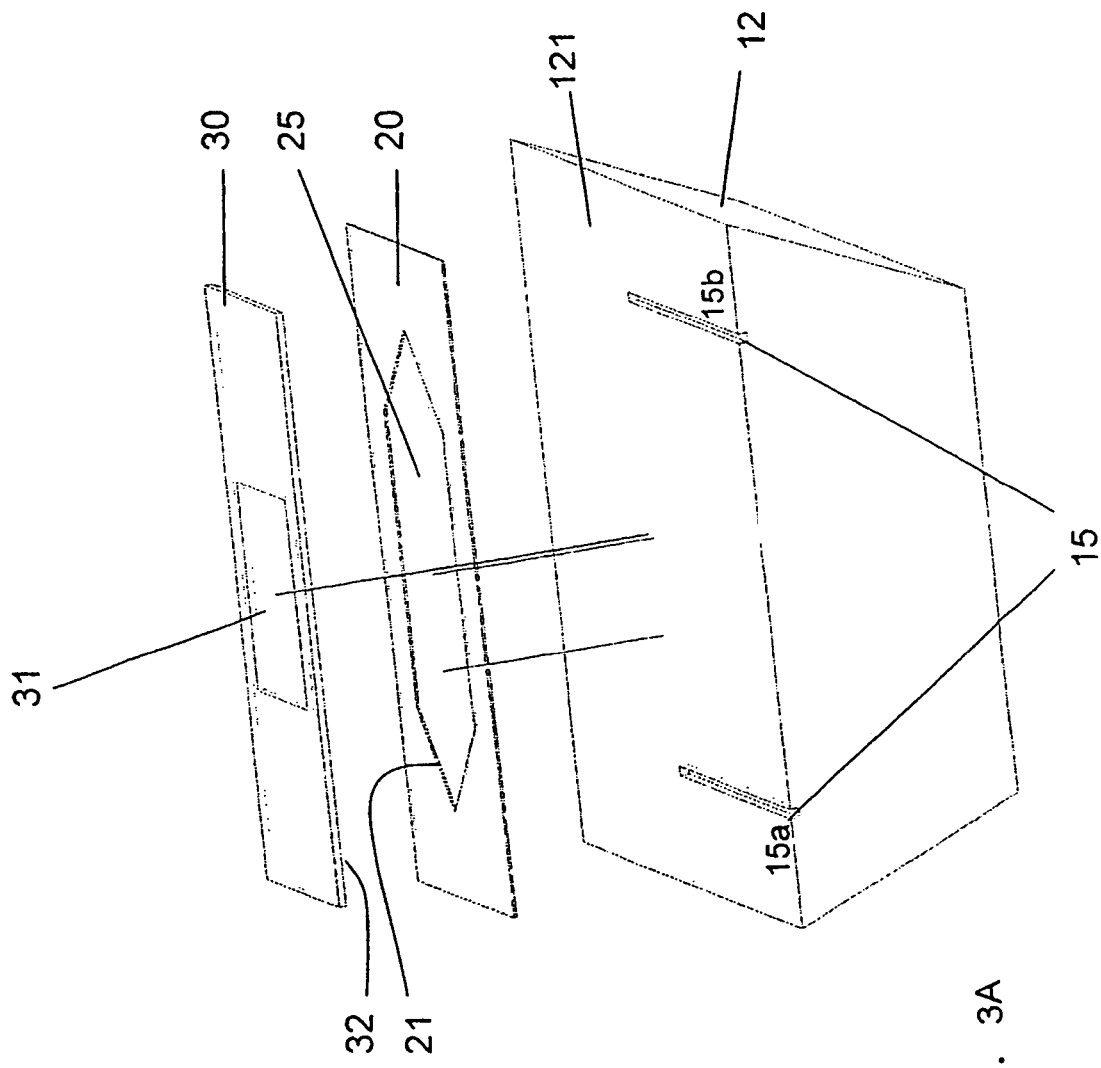
FIG. 3A shows individual elements of a device according to a first embodiment of the invention.

Detailed examples will now be described. FIG. 3A shows elements of a device according to the invention. Reference number 12 refers to a first optical element shown as a prism.

Reference number 30 refers to a second optical element shown as a platelet. The first optical element 12 has a first radiation penetration surface 121, and the second optical element 30 has an opposite second radiation penetration surface 32. Optical coupling is to take place between the first and second optical elements via the respective radiation penetration surfaces.

An intermediate element 20 having a space 25 is provided between the first optical element 12 and the second optical element 30. Said space 25 defines a side wall 21 in the intermediate piece 20. Furthermore, channels 15 are provided in the first optical element 12 through which index-adapting liquid or gas may flow.

According to this embodiment, the intermediate piece 20 and the second optical element 30 are placed on the first optical element 12 in such a manner that the space 25 forms a chamber in which the channels 15a, 15b respectively form a feeding or discharge conduit. The circumferentially closed side wall 21, a first section of the first radiation penetration surface 121, formed by projection of the side wall 21 on the first radiation penetration surface 121, and a second section of the second radiation penetration surface 32, formed by projection of the circumferentially closed sidewall 21 on the second radiation penetration surface 32, form a chamber which is closed except for the feeding and discharge conduits.

The expression "circumferentially closed" means in this regard that the projection of the side wall defines a closed circumferential line.

Index-adapting liquid can be filled into this chamber for the purpose of adapting the index between the first optical element 12 and the second optical element 30. Supply and discharge can thereby occur through one channel, the other channel then being used purely for the purpose of air escape, or one channel can be used for supply and the other for discharge of the index-adapting liquid so as to form some sort of flow cell.

The channels 15a, 15b shown in the Figure can be produced in the first optical element 12 in any suitable manner, for example by ultrasound machining, sawing or milling or also by using photolithographic means. Although the channels 15a, 15b are preferably formed in the first optical element 12, as shown in FIG. 3A, they can also be formed individually or jointly in the intermediate element 20 or the second optical element 30. Thus, one or both of the channels might be formed in the intermediate element 20 and might enter the chamber through the side wall 21.

The intermediate element 20 can be made of any suitable material such as, for example, glass. The space 25 of the intermediate element 20 preferably has the cross-sectional shape shown in FIG. 3A, namely a rectangular center portion and two triangular end portions which cooperate with the channels such that the tips of the triangular end portions respectively face the feeding conduit 15a or the discharge conduit 15b (see also FIG. 3B). In other words, the cross-section of the space 25 preferably has a double-trapezoid shape.

The space can be produced by any suitable method, for example by laser machining or punching, depending on the material selected for the intermediate element 20. The V-shaped tips of the double trapezoid lie as exactly as possible on the ends of the channels 15a, 15b, such that there the index-adapting liquid (e.g. index oil) can flow through the respective channel and into or out of the chamber between the first optical element 12 and the second optical element 30.

The thickness of the intermediate element 20 is such that the capillary action of the delimiting surfaces (the first section in the first radiation penetration surface, the second section in the second radiation penetration surface and the side wall 21) is so low that the index-adapting liquid can flow without major resistance and/or that the liquid transportation is not determined to a dominant extent by capillary forces.

The intermediate element 20 is preferably adhered onto the first optical element 12 so as to form a permanent unit from the first optical element and the intermediate element 20 since in this manner the tips of the double trapezoid need to be adjusted only once in relation to the two channels 15a, 15b.

The second optical element 30, which is preferably a platelet carrying a measurement sample to be analyzed using radiation, is preferably detachably placed on the intermediate element 20. This can be done, for example, by means of an assembly including spring clips.

FIG. 7 shows an alternative to the embodiment in FIG. 3a. FIG. 7 shows, in turn, a first optical element 12 (e.g. a prism) with a first radiation penetration surface 121, as well as a second optical element 30 (e.g. a platelet with a sensor area or measurement sample 31) having a second radiation penetration surface 32 which is opposite to the first radiation penetration surface 121.

In the example of FIG. 7, the first optical element 12 has a groove 26. The groove has a side wall 21, with the bottom of the groove 26 and the side wall 21 forming, together with the remaining surface of the first optical element 12 facing the second optical element 30, the (complete) radiation penetration surface 121. In other words, the bottom of the groove 26 is part of the radiation penetration surface 121, the radiation penetration surface 121 being thus disposed, however, in two different planes.

The channels 15a, 15b lead into the groove 26, and therefore, if the second optical element 30 is placed (preferably detachably) on the first optical element 12, a chamber is defined by the groove 26, said chamber being closed except for the channels 15a, 15b so as to hold index-adapting liquid and to thus optically couple the first to the second optical element. In other words, the section in the surface of the first optical element 12 which is defined by the side wall 21 is smaller than the complete surface, as can be seen in FIG. 7, however, the second section which is defined by projection of the side wall 21 on the second optical element 30 is also smaller than the surface area of the second radiation penetration surface 32 on the second optical element 30.

The materials and manufacturing techniques to be used in the example of FIG. 7 are the same as those in the example of FIG. 3A. It should be noted that the configurations of FIGS. 3A and 7 can also be combined, i.e. a chamber can be formed both by a groove 26 and a space 25 in an intermediate element 20 such that the chamber is formed in each case in part by the groove and in part by the space.

In FIG. 7, the cross-sectional shape of the groove 26 is illustrated as being oval. The cross-section could also have the double-trapezoid shape of the space 25 of the intermediate element 20 in FIG. 3A; it is possible just as well for the space 25 in FIG. 3A to have the oval shape of the groove 26 in FIG. 7. In principle, the cross-section of the space 25 or the groove 26 can be selected to have any suitable shape, the double-trapezoid shape shown in FIG. 3A being, however, preferred since it ensures an improved supply and discharge of index-adapting liquid.

As already mentioned, the second optical element 30 is preferably mounted so as to be detachable. It should be noted that this will normally result in a small gap between the second optical element 30 and the surface 121 (in the example of FIG. 7) or the intermediate element 20 (in the example of FIG. 3A), with the capillary forces in this small gap preventing, however, the index-adapting liquid from passing through, thus forming nonetheless a chamber which is closed at least for the index-adapting liquid.

Figure 3B:
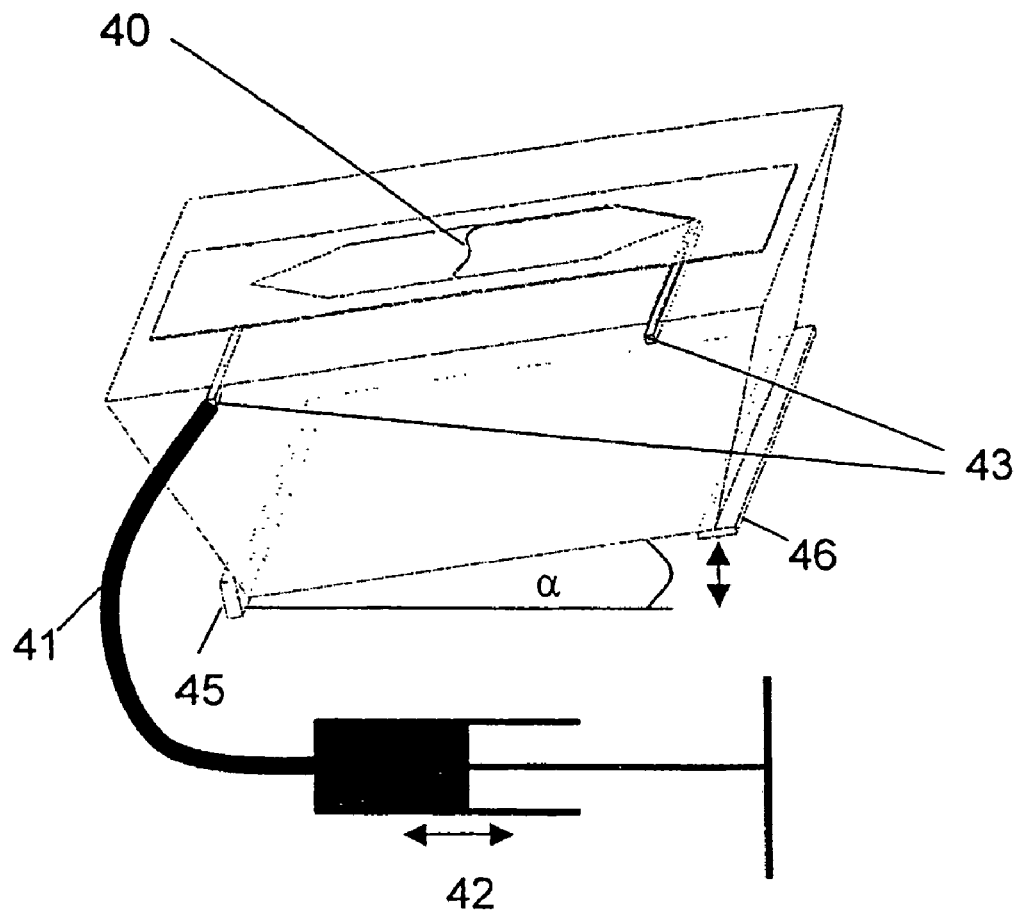
FIG. 3B shows the composed elements of FIG. 3A and explains the operation according to a preferred embodiment.

FIG. 3B shows an arrangement in which the individual elements shown in FIG. 3A are joined, and additionally shows a supply means 41, 42, 43 for supplying index-adapting liquid, as well as elements 45, 46 which represent a tilting means with which the complete array can be tilted at an angle α such that the point of supply of index-adapting liquid is disposed, as viewed in the direction of gravity, at a level lower than the point of discharge. The supply device can be formed, for example, by a reciprocable syringe 42, a tube 41 and one or two cannulae 43, said cannulae 43 being inserted in the channels 15a, 15b (see FIG. 3A).

The elements 45 and 46 are illustrated only schematically, with 45 being a stop and 46 an element for lifting the first optical element 12, for example by means of an electric motor (not shown). The tilting of the array at an angle α ensures that a horizontal liquid front 40 is formed as a result of gravity and that the air (or the gas present in the chamber) can escape in a defined manner through the channel 15b situated farther above.

The index-adapting liquid can be removed again upon termination of measurements either by being drawn back into the syringe 42 or by air being pressed through the chamber, thus expelling the index-adapting liquid from the outlet channel 15b. The entire filling and emptying process with index-adapting liquid can be easily automated using motorized syringe drives.

As already mentioned previously, the second optical element 30 is preferably a carrier comprising one or more sensor fields 31. Although the Figures, to provide greater clarity, show only one sensor field 31, the second optical element 30 can, of course, also carry more such fields. These fields can be, for example, SPR sensor fields, i.e. sensor fields provided on the side of the optical element 30 facing away from the second radiation penetration surface 32. A thin layer suitable for SPR (e.g. gold) is applied to this side facing away, on which, in turn, specific ligands are immobilized. Measurement occurs by illuminating the sensor fields from the body of the platelet 30.

The arrangement of the one or more sensor fields 31, the dimensions of the groove 26 or space 25 and the supply of radiation to the first optical element are preferably such that the entire surface of the one or more sensor fields 31 is illuminated from the body of the second optical element 30 and that the light reflected from this area can completely exit the prism. In other words, the space 25 should be dimensioned to be so large that it does not act as a screen with regard to the sensor field 31.

It should be noted that the supply means 41, 42, 43 and the tilting means 45, 46 can also be used in the configuration of FIG. 7 in order to achieve the same effects. It is possible by means of the arrangements described above to achieve a defined, bubble-free and conveniently automatable filling of index-adapting liquid into a chamber connecting the first and second optical elements. This presents an advantage especially in connection with the use of sensor plates as the second optical element that are detachably mounted on the array, since index-adapting liquid can be conveniently filled into the chamber after mounting of the sensor plate and can be removed therefrom again after measurement, whereupon the sensor plate can be removed and a new measurement can be started, for example by mounting another sensor plate.

Figure 4A:
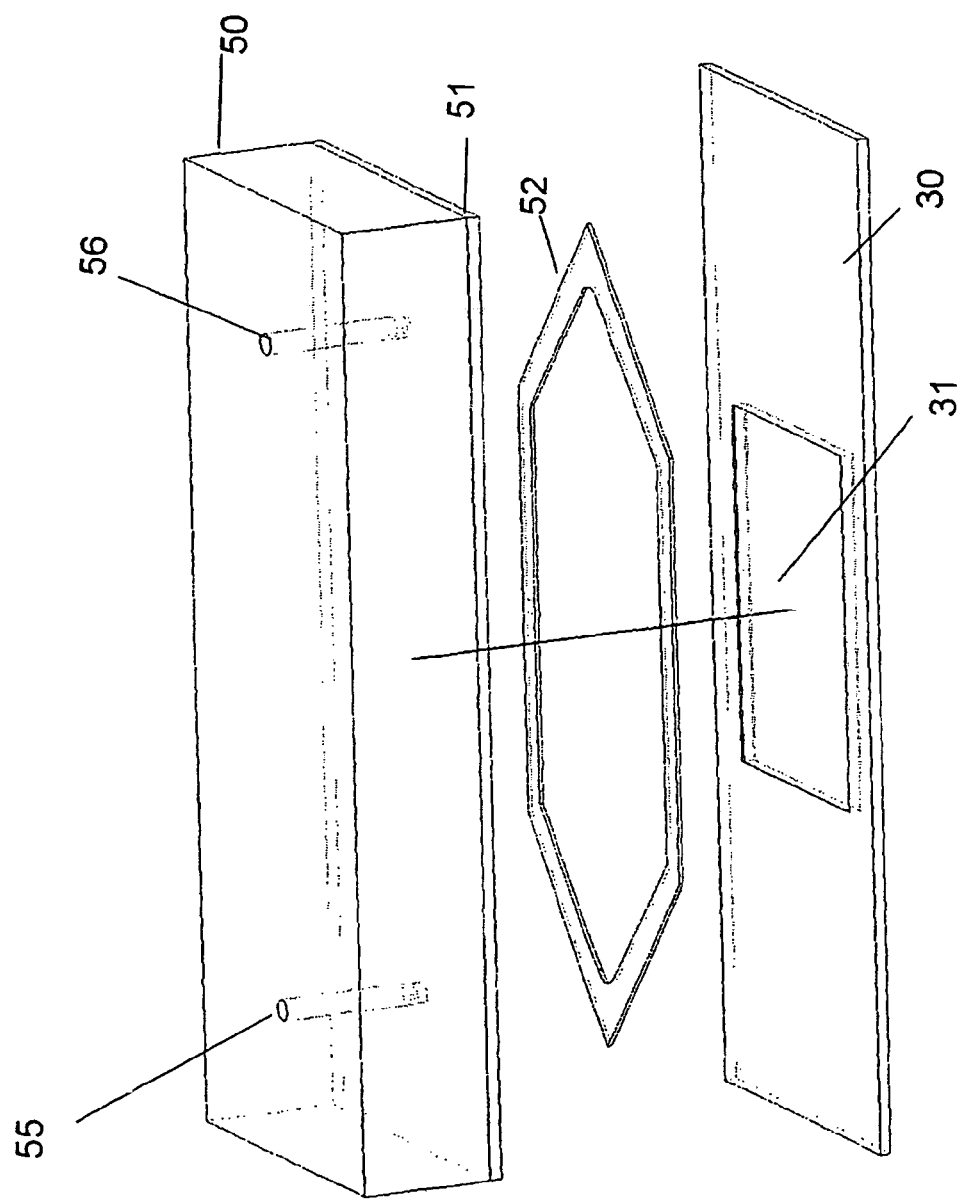
FIG. 4A shows elements of an array for supplying sample liquid onto a sensor area of the second optical element.
Figure 4B:
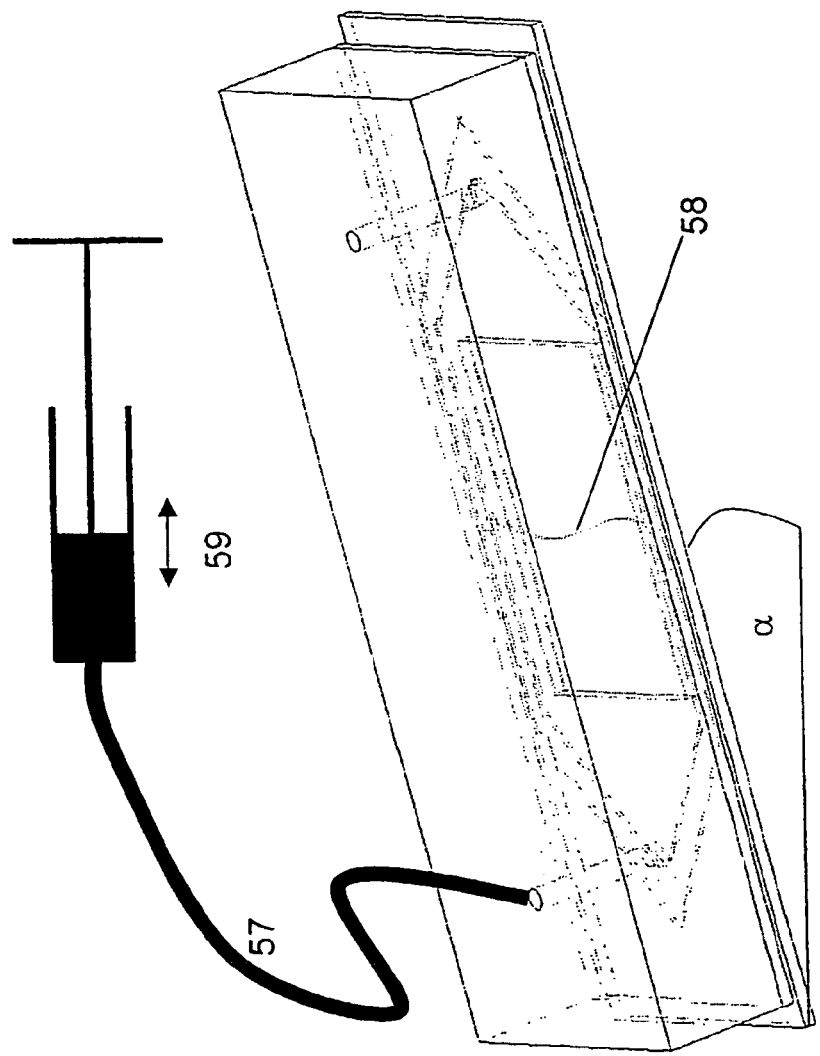
FIG. 4B shows the composed elements of FIG. 4A explaining a preferred operating method.

In case that a sensor plate, for example an SPR sensor plate having sensor fields on the side facing away from the second radiation penetration surface 32, is used as the second optical element, additional elements are preferably provided, as shown in FIGS. 4A and 4B. A thermostatable block 50 with a first fluid-conducting channel 55 and a second fluid-conducting channel 56, as well as a gasket 52 are disposed on the side of the plate 30 having one or more sensor fields 31. The gasket 52 surrounds the one or more sensor fields 31 and thus cooperates with the thermostatable block 50 such that a space is formed around the one or more sensor fields in which sample liquid intended for interaction with the one or more sensor fields 31 can be fed or discharged through the first fluid-conducting channel 55 and/or the second fluid-conducting channel 56. The formed space thereby presents some kind of flow cell for sample liquid.

As shown in FIG. 4B, the use of this system is particularly preferred in combination with the already described tilting means since the point of supply of sample liquid can then be set lower, as viewed in the direction of gravity, than the point of discharge and/or air escape so as to permit bubble-free supply of sample liquid.

The thermostatable block 50 can be, for example, a metal block with an inert coating 51. Thermostatting of the metal block can take place by means of either a Peltier element or additional bores in the metal block and a circulation thermostat. The gasket 52, which has preferably the cross-section of a double-trapezoid, borders the one or more sensor fields 31 on the plate 30. The metal block has bores 55 and 56 as fluid-conducting channels. These bores are designed to match the V-shaped corners above the gasket 52. The coating 51 can be implemented in any suitable manner, for example using PTFE, or it can be realized as a thin glass platelet which is adhered onto the metal block and likewise has through-holes at the locations of the bores 55 and 56.

The thickness of the gasket 52 defines the layer thickness of the resulting space which is delimited at the top by the metal block and at the bottom by the sensor plate 30. Sample liquid is introduced into the bore 55 via a sheathed line 57 and a syringe 59. As already described, the angle of inclination/tilt angle α ensures that a horizontal liquid front 58 is formed in the flow cell so as to prevent bubble formation. The expelled air escapes from the outlet 56, which is thus designed as an air escape connection. The gasket is preferably dimensioned such that no substantial capillary forces arise in order that the flow of sample liquid into the resulting space is not impeded to a substantial extent, thus enabling quick liquid transportation.

The space can be emptied by the liquid being drawn back into the syringe 59 or by air being pressed through the supply channel 55 in order to expel the sample liquid from the second conducting channel 56. It is also possible to expel a specific sample liquid by supplying another sample liquid or a specific rinsing liquid (e.g. pure water).

The combination of the arrays according to FIG. 3 or 7 with the array according to FIG. 4 permits a particularly preferred implementation of a measuring apparatus, in particular an SPR measuring apparatus. For this, it is possible to move both the index-adapting liquid and the various sample liquids using automated syringe drives.

A schematic view of a complete measurement array is shown in illustration 5. The array is adapted to allow several different sample liquids to be sequentially washed over the one or more sensor fields 31. For example, this may be first a reference buffer, then a sample liquid, then again a reference buffer, a sample liquid, etc., with one measurement being carried out for each liquid by recording a spectrum (e.g. an SPR spectrum) to characterize the interactions between the respective sample liquid and the one or more sensor fields.

Figure 5:
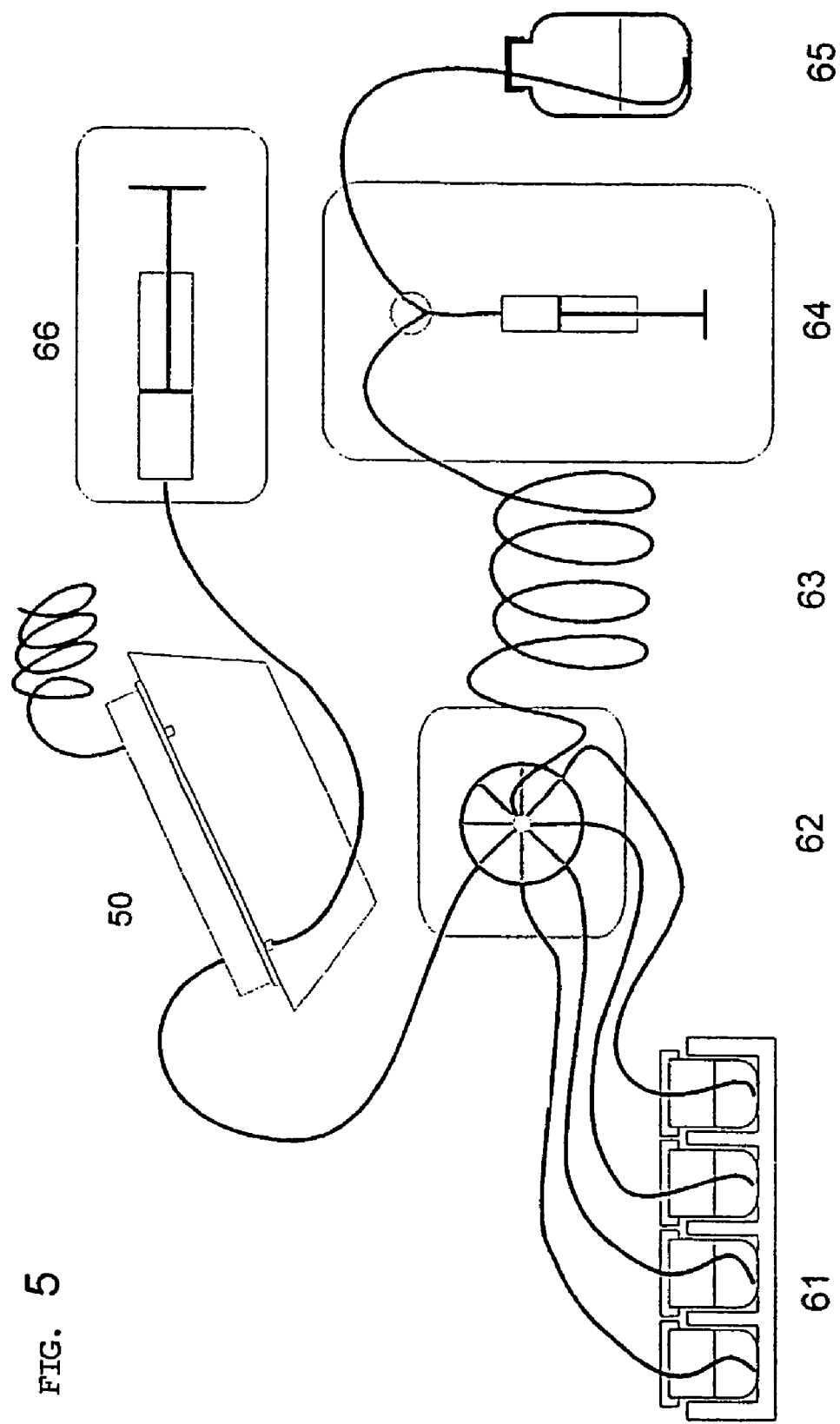
FIG. 5 shows a complete measurement set-up with several sample vessels.

In the schematic measurement array of FIG. 5, syringe drives with a three-way valve 64 (also called diluter) and a multivalve 62 are used for the purpose of automation. Furthermore, a container with system liquid 65, a tube reservoir 62 and sample vessels 61 are provided. At the start of measurement, system liquid is initially filled, by switching over the three-way valve 64 or the multivalve 62, into the tube reservoir 63 and the tubes to the samples 61 via the three-way valve 64. Thereafter, the tubes are hung in the sample vessels 61. The first sample liquid can now be drawn up into the tube reservoir and can then be introduced into the space formed above the one or more sensor fields 31. Following measurement, the liquid can be withdrawn from the space and the second sample liquid can be introduced so as to enable the second measurement. Alternatively, the first liquid can also be displaced from the outlet by supplying the second sample liquid.

Filling of the chamber for index-adapting liquid occurs by means of a further syringe pump 66.

As already mentioned previously, the device according to the invention is preferably used for SPR measurements. The optical assembly for such measurements will now be shown with reference to FIG. 6.

Figure 6:
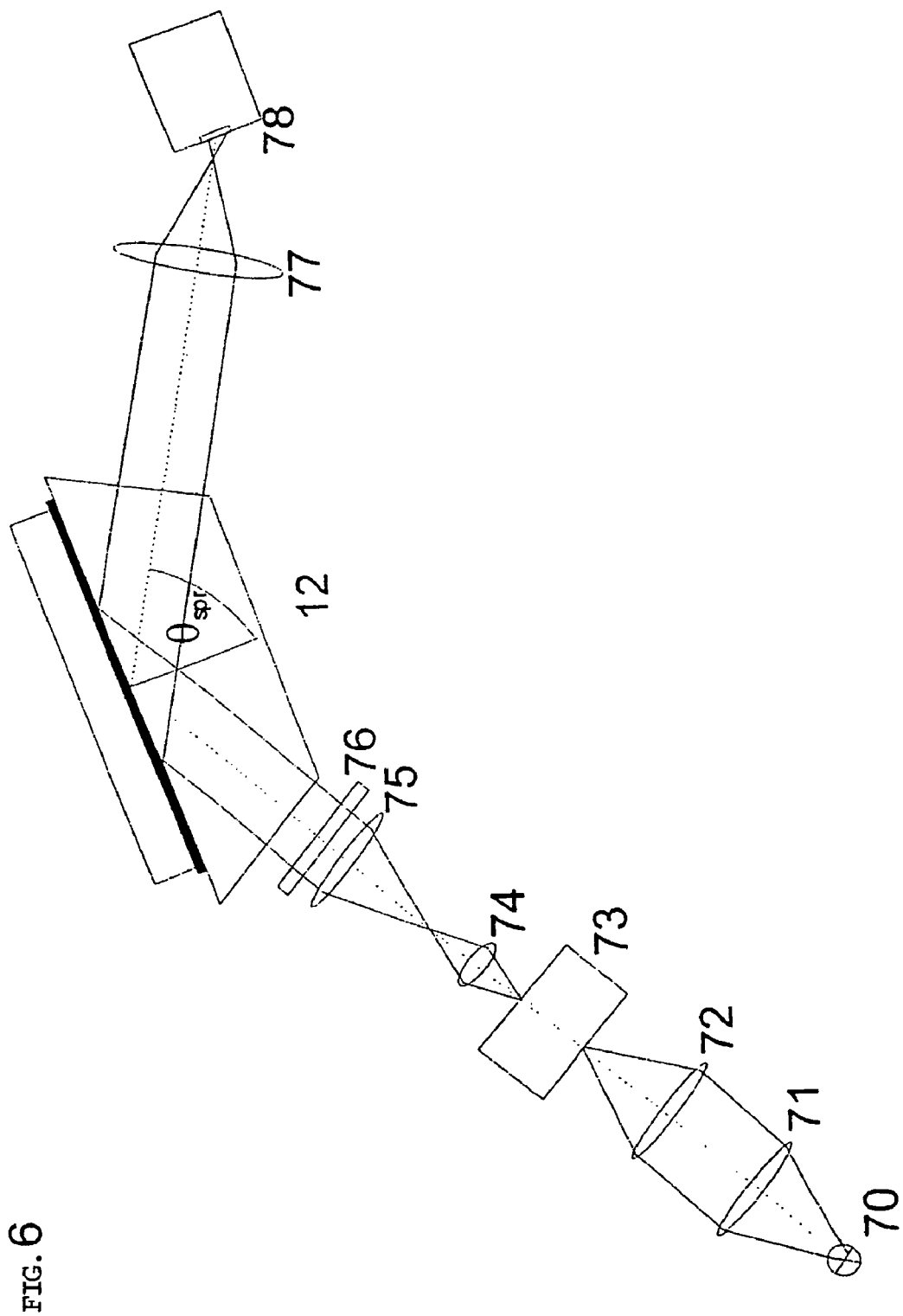
FIG. 6 is a schematic view of the radiation path for feeding radiation to the first and second optical elements or for removing it therefrom.

FIG. 6 shows an optical assembly which makes it possible to detect a refractive index change in a liquid layer above the gold surface—caused, for example, by the attachment of one partner in solution to the other partner immobilized on the surface—using the means described above consisting of thermostating block, sensor plate and prism. The assembly corresponds for the most part to the arrangement described in WO 01/63256 A1.

The assembly has the purpose of measuring the wavelength-dependent surface plasmon resonance in the form of reflection spectra.

For this, the white light from a lamp 70 is collimated using an optical system 71 and is coupled into the monochromator 73 using an optical system 72.

The light exiting the monochromator in a cone is transformed via the optical systems 74 and 75 into a light bundle having a cross-section large enough to completely light the active field 31 on the plate 30.

After passing through a polarizer 76, the light is polarized, i.e. the field vector of the light oscillates parallel to the plane of incidence, which is a prerequisite for observing SPR. Optical fibers or fold mirrors can also be used in the illumination ray path described so far, e.g. between 71 and 72 or between 73 and 74, in order to simplify a convenient structure of the measurement means.

The collimated light passes through the left side of the prism 12, is then reflected from the gold layer of the sensor and then exits through the right side 12 of the prism. The sensor surface is imaged on a CCD detector 78 (or e.g. an InGaAs detector) through an optical system 77. Since imaging of the sensor surface is to take place at the angle $\theta_{sprt}$, the detector surface should preferably not be oriented perpendicularly to the optical axis but rather inclined thereto. In order to obtain a clearly focused image of the entire sensor surface, the angle of inclination should meet the Scheimpflug condition.

The general aspects regarding surface plasmon resonance have already been described in the introduction and do not, therefore, have to be repeated here.

Although the present invention has been described with reference to surface plasmon resonance as the preferred application, the invention is not limited thereto. It can rather be used for optically coupling any optical elements. Even in those cases where it is to be used for coupling sensor plates as the second optical element, its application is not limited to surface plasmon resonance but it can rather be employed in any measuring principle in which the illumination of samples and/or sensor surfaces on the second optical element is of interest.

The invention claimed is:

1. A device for optically coupling a first optical element to a second optical element, comprising:
   a first optical element having a first radiation penetration surface, the first optical element comprising a prism;
   a second optical element having a second radiation penetration surface which is opposite the first radiation penetration surface, the second optical element having one or more sensor fields;
   a chamber between the first and second radiation penetration surfaces, the chamber closed by a circumferential side wall which connects the first and second radiation penetration surfaces and the chamber closed except for openings for a feeding conduit and a discharge conduit, the feeding conduit to the chamber configured to supply index-adapting liquid and the discharge conduit from the chamber configured to evacuate index-adapting liquid or gas from the chamber,
   the circumferential side wall defining a first section in the first radiation penetration surface and a second section in the second radiation penetration surface, the surface area of the first section being smaller than the surface area of the first radiation penetration surface, and the surface area of the second section being smaller than the surface area of the second radiation penetration surface.

2. The device according to claim 1, wherein the feeding conduit and the discharge conduit are configured as channels in the first optical element.

3. The device according to claim 1, wherein the chamber is formed, as a whole or in part, by a groove in the first optical element.

4. The device according to claim 1, wherein the chamber is formed, as a whole or in part, by a space in an intermediate element which is situated, during optical coupling, between the first and second optical elements.

5. The device according to claim 1, wherein the cross-section of the chamber comprises a rectangular center portion and two triangular end portions, with the tips of the triangular end portions respectively facing the feeding conduit or the discharge conduit.

6. The device according to claim 1, wherein the second optical element comprises one or more sensor fields.

7. The device according to claim 6, wherein the second optical element is an SPR sensor plate and the one or more sensor fields are SPR sensor fields.

8. The device according to claim 6 wherein the one or more sensor fields are disposed on the side of the second optical element facing away from the second radiation penetration surface.

9. The device according to claim 6, wherein a radiation supply device is configured to couple radiation into the first optical element such that the entire surface of the one or more sensor fields is illuminated from the body of the second optical element.

10. The device according to claim 8 wherein a thermostatable block having a first fluid-conducting channel and a second fluid-conducting channel, and a gasket, said gasket surrounding the one or more sensor fields and cooperating with the thermostatable block so that a space is formed around the one or more sensor fields in which sample liquid can be fed or discharged through the first fluid-conducting channel and/or the second fluid-conducting channel.

11. The device according to claim 10, comprising a device for supplying and discharging sample liquid, the device being connected with the first fluid-conducting channel, and the second fluid-conducting channel being designed as an air escape connection.

* * * * *